United States Patent
Shigeta

(10) Patent No.: US 12,251,475 B2
(45) Date of Patent: Mar. 18, 2025

(54) SOLID PHARMACEUTICAL FORMULATIONS OF ASIMADOLINE

(71) Applicant: Tioga Pharmaceuticals, Inc., San Diego, CA (US)

(72) Inventor: Kosuke Shigeta, Osaka (JP)

(73) Assignee: Tioga Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 16/448,927

(22) Filed: Jun. 21, 2019

(65) Prior Publication Data

US 2020/0009061 A1   Jan. 9, 2020

Related U.S. Application Data

(63) Continuation of application No. PCT/US2017/067655, filed on Dec. 20, 2017.

(60) Provisional application No. 62/442,803, filed on Jan. 5, 2017, provisional application No. 62/437,603, filed on Dec. 21, 2016.

(51) Int. Cl.
*A61K 9/20* (2006.01)
*A61K 9/28* (2006.01)
*A61K 31/40* (2006.01)

(52) U.S. Cl.
CPC .......... *A61K 9/2018* (2013.01); *A61K 9/2009* (2013.01); *A61K 9/2054* (2013.01); *A61K 9/2095* (2013.01); *A61K 9/2813* (2013.01); *A61K 31/40* (2013.01)

(58) Field of Classification Search
None
See application file for complete search history.

(56) References Cited

U.S. PATENT DOCUMENTS

| | | | |
|---|---|---|---|
| 5,532,266 A | 7/1996 | Gottschlich et al. | |
| 5,776,972 A | 7/1998 | Barber et al. | |
| 6,004,964 A | 12/1999 | Farrar et al. | |
| 6,060,504 A * | 5/2000 | Stein | C07D 207/12 514/428 |
| 6,060,964 A | 5/2000 | Baier et al. | |
| 7,960,429 B2 | 6/2011 | Mangel | |
| 8,168,218 B2 * | 5/2012 | Vergnault | A61K 9/0002 424/464 |
| 2004/0266806 A1 | 12/2004 | Sanghvi et al. | |
| 2006/0018933 A1 | 1/2006 | Vaya et al. | |
| 2008/0152595 A1 * | 6/2008 | Emigh | A61K 9/4866 424/10.4 |
| 2011/0046174 A1 | 2/2011 | Mangel | |
| 2011/0195989 A1 * | 8/2011 | Rudnic | A61K 31/485 514/282 |
| 2012/0088786 A1 * | 4/2012 | Dadagher | A61K 31/485 514/282 |

FOREIGN PATENT DOCUMENTS

| | | | | |
|---|---|---|---|---|
| EP | 2682104 A1 * | 1/2014 | | A61K 31/192 |
| JP | 2006117694 A * | 5/2006 | | |
| WO | WO-2004/054970 | 7/2004 | | |
| WO | WO-2011/010214 | 1/2011 | | |
| WO | WO-2013128276 A2 * | 9/2013 | | A61K 31/485 |

OTHER PUBLICATIONS van Kamp et al., Studies on tableting properties of lactose. IV. Dissolution and disintegration properties of different types of crystalline lactose, 1986, International Journal of Pharmaceutic., vol. 28, pp. 229-238. (Year: 1986).*
Rowe et al., The refractive indices of polymer film formers, pigments and additives used in tablet film coating: their significance and practical application, 1982, J. Pharm. Pharmacol., vol. 35, pp. 205-207. (Year: 1982).*
Berge et al., "Pharmaceutical Salts," J Pharm Sci (1977) 66(1):1-19.
Smith et al., "The colouration of tablets and capsules," Manufacturing Chemist (2010) Retrieved from https://www.manufacturingchemist.com/news/article_page/The_colouration_of_tablets_and_capsules/34905.
Philippe et al., "Mu opioid receptor expression is increased in inflammatory bowel diseases: implications for homeostatic intestinal inflammation," Gut (2006) 55:815-823.
Szalwinska et al., "IBS-Symptoms in IBD Patients—Manifestation of Concomitant or Different Entities," J Clin Med (2021) 10:31.

* cited by examiner

*Primary Examiner* — H. Sarah Park
(74) *Attorney, Agent, or Firm* — MORRISON & FOERSTER LLP

(57) ABSTRACT

The present invention relates to solid, oral dosage forms of asimadoline comprising lactose monohydrate.

12 Claims, No Drawings

SOLID PHARMACEUTICAL FORMULATIONS OF ASIMADOLINE

CROSS-REFERENCE TO RELATED APPLICATIONS

This application is a U.S. continuation of PCT/US2017/067655 filed Dec. 20, 2017 which claims priority to U.S. Provisional Application No. 62/437,603, filed Dec. 21, 2016, and U.S. Provisional Application No. 62/442,803, filed Jan. 5, 2017 which are hereby incorporated by reference in their entirety.

TECHNICAL FIELD

The present invention relates to solid dosage formulations of N-methyl-N-[(1S)-1-phenyl-2-((3S)-3-hydroxypyrrolidin-1-yl)ethyl]-2,2-diphenylacetamide (asimadoline) or a pharmaceutically acceptable salt thereof, and methods of making and using such formulations.

BACKGROUND

Asimadoline, or N-methyl-N-[(1S)-1-phenyl-2-((3S)-3-hydroxypyrrolidin-1-yl)ethyl]-2,2-diphenylacetamide, is a peripherally selective, kappa-opioid receptor agonist known to exhibit antipruritic, analgesic, neuroprotective, anti-inflammatory, antiasthmatic, diuretic, anticonvulsive, and antitussive actions.

Asimadoline has been described for the treatment of hyperalgesia (in particular, inflammation-related hyperalgesia), cerebral edema, hypoxia, ischemic damage, pain, hypersensitivity to pain, neurodermatitis, disorders of intestinal motility, postoperative ileus, itch, pruritus, allergic skin disorders, rheumatic disorders, inflammatory bowel disorders, irritable bowel syndrome (IBS, including diarrhea-predominant and alternating constipation and diarrhea forms (IBS-D and IBS-A)), diarrhea, nausea, dyspepsia (including dyspepsia not associated with an ulcer), functional intestinal diseases (including functional abdominal pain, functional wind or flatulence, functional obstipation, constipation, blockage), chronic motility disorders, and neuropathy (including peripheral neuropathy and diabetic neuropathy). U.S. Pat. Nos. 5,532,266; 6,060,504; 7,960,429 (IBS); PCT Publ. No. WO2004/054970.

There is a need for a solid dosage formulation for oral administration with suitable pharmaceutical properties. A formulation prepared from 1 kg of active ingredient, 4 kg of lactose (61.5%), 1.2 kg of potato starch (18.5%), 0.2 kg of talc (3%), and 0.1 kg of magnesium stearate (1.5%), compressed into tablets containing 10 mg of active ingredient. See U.S. Pat. Nos. 5,532,266, 5,776,972, 6,060,504. U.S. Pat. No. 7,960,429 describes a tablet formulation with 0.15, 0.5, or 1.0 mg asimadoline plus lactose, microcrystalline cellulose, hypromellose, croscarmellose sodium, magnesium stearate, Macrogol 400 (polyethylene glycol), Dimethicone 100 (dimethicone), titanium dioxide, and iron oxide red ($Fe_2O_3$).

Certain asimadoline pharmaceutical compositions with improved stability and other improved pharmaceutical properties are described herein.

SUMMARY OF THE INVENTION

In one aspect, the invention relates to a pharmaceutical composition comprising asimadoline or a pharmaceutically acceptable salt thereof, lactose monohydrate, and less than 5% w/w water. The invention also relates to a pharmaceutical composition as described herein for use as a medicament.

In another aspect, the invention relates to a method of treating a disease or condition mediated by kappa-opioid receptor activity, comprising administering to a subject in need of such treatment an effective amount of a pharmaceutical composition as described herein. In another aspect, the invention is directed to a use of a pharmaceutical composition as described herein as a medicament for the treatment of a disease or condition mediated by kappa-opioid receptor activity. In some aspects, the disease or condition mediated by kappa-opioid receptor activity is pruritus.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION OF THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Asimadoline is a compound with the chemical name of N-methyl-N-[(1S)-1-phenyl-2-((3S)-3-hydroxypyrrolidin-1-yl)ethyl]-2,2-diphenylacetamide. The structure of asimadoline is shown below.

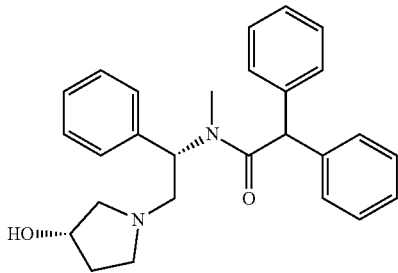 [SMILES: CN(C(=O)C(c1ccccc1)c1ccccc1)[C@H](CN1CC[C@H](O)C1)c1ccccc1]

Asimadoline hydrochloride exists in various crystalline polymorphs, including Forms II and IV (see U.S. Pat. No. 6,060,504).

Except as otherwise noted, the methods and techniques of the present embodiments are generally performed according to conventional methods well known in the art and as described in various general and more specific references that are cited and discussed throughout the present specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to particular formulation ingredients or amounts of formulation ingredients are specifically embraced by the present invention and are disclosed herein just as if each and every combination was individually and explicitly disclosed.

Representative Embodiments

The present invention is directed to a pharmaceutical composition comprising asimadoline or a pharmaceutically acceptable salt thereof and lactose monohydrate. In some embodiments, the composition comprises less than about 5% w/w of a cellulose or starch excipient. In some embodiments, the composition lacks microcrystalline cellulose and/or hypromellose (hydroxypropyl methylcellulose). In other embodiments, the composition lacks one or more of sodium starch glycolate, cross-linked sodium carboxymethyl starch, cornstarch, and hypromellose.

In some embodiments, the pharmaceutically acceptable salt of asimadoline is asimadoline hydrochloride. In some embodiments, the asimadoline hydrochloride is in crystalline form. In other embodiments, the crystalline asimadoline is in Form II or is in Form IV. In some embodiments, the composition comprises from about 0.1 to about 10.0 mg, or about 0.1 to about 5.0 mg, or about 0.25 to about 5.0 mg, or about 0.25 to about 3.0 mg, or about 0.4 to about 3.0 mg, or about 2.3 to about 3.0 mg, or about 0.5 mg, or about 2.5 to about 2.8 mg of asimadoline (or a therapeutically equivalent amount of a pharmaceutically acceptable salt thereof) per dosage unit (e.g., per tablet). In some embodiments, asimadoline drug loading is about 1 to about 3% by weight (based on the molecular weight of asimadoline free base), or is about 1.5 to about 2.5% by weight, relative to the tablet core (or raw tablet) weight. For example, in some embodiments, asimadoline drug loading is about 2.0%, about 2.5%, or about 3.0%, relative to the tablet core (or raw tablet) weight. In some embodiments, asimadoline drug loading is 2.5% in a 100 mg tablet core (or raw tablet).

A "pharmaceutically acceptable salt" of asimadoline is a salt form that is non-toxic, biologically tolerable, or otherwise biologically suitable for administration to the subject. See, generally, Berge et al., "Pharmaceutical Salts," *J. Pharm. Sci.* 1977, 66, 1-19. Preferred pharmaceutically acceptable salts are those that are pharmacologically effective and suitable for contact with the tissues of subjects without undue toxicity, irritation, or allergic response.

Examples of pharmaceutically acceptable salts of asimadoline include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Other suitable pharmaceutically acceptable salts are known to one of ordinary skill in the art. In some embodiments, the salt form is asimadoline hydrochloride salt.

A pharmaceutically acceptable salt of asimadoline may be prepared by any suitable method available in the art, for example, treatment of asimadoline with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids, and any other acid and mixture thereof that are regarded as equivalents or acceptable substitutes in light of the ordinary level of skill in this technology.

In some embodiments, the lactose monohydrate is spray-dried lactose monohydrate or is granulated lactose monohydrate, or is a mixture thereof. In some embodiments, the granulated lactose monohydrate has a particle size distribution of at least 99% less than 250 μm, at least 96% less than 150 µm, at least 90% less than 100 µm, and/or 50-65% less than 45 µm (e.g., Pharmatose 200M, DMV-Fonterra). In some embodiments, the spray-dried lactose monohydrate has a particle size distribution of no more than 15% less than 45 µm, 30-60% less than 100 µm, and/or at least 98% less than 250 µm (e.g., SuperTab 11SD, DMV-Fonterra). Particle size distribution may be measured by any suitable method known to one of ordinary skill in the art such as, for example, sifting methods, such as air jet sieve or sonic sifter, or light scattering methods, such as laser light scattering.

In some embodiments, the lactose monohydrate is about 80 to about 97% by weight, or about 85 to about 97% by weight, or about 85 to 90% by weight, or about 90 to about 97% by weight, or about 92 to about 97% by weight, or about 93 to about 96% by weight of the composition. In some embodiments, the composition comprises from about 7 to about 15% by weight, or about 8 to about 12% by weight, or about 9 to about 10% by weight, or about 9.5% by weight of granulated lactose monohydrate. In other embodiments, the composition comprises from about 60 to about 90% by weight, or about 70 to about 90% by weight, or about 80 to about 90% by weight, or about 83 to about 88% by weight of spray-dried lactose monohydrate.

In some embodiments, the asimadoline or a pharmaceutically acceptable salt and spray-dried lactose monohydrate together at a total amount of about 85 to about 88%, or about 86 to about 87%, or about 86.6 to 87%, or about 86.8% of the composition by weight. In other embodiments, the amount of asimadoline or a pharmaceutically acceptable salt thereof and total lactose monohydrate is from about 90 to about 97% by weight, or about 92 to about 97% by weight, or about 95 to about 97% by weight, or about 95% by weight, or about 96% by weight, or about 96.1%, 96.2%, 96.3%, 96.4%, or 96.5% by weight, or about 97% by weight.

In some embodiments, the composition further comprises a disintegrant. In some embodiments, the disintegrant is croscarmellose sodium (e.g., an internally cross-linked sodium carboxymethylcellulose disintegrant such as Kiccolate ND-2HS, Asahi Kasei Chemicals) or crospovidone (cross linked polyvinyl N-pyrrolidine, or PVP). In some embodiments, the composition comprises about 1 to about 10% by weight, or about 1 to about 5% by weight, or about 2 to about 4% by weight, or about 3% by weight, or about 2.7%, 2.8%, 2.9%, 3.0%, 3.1%, 3.2%, or 3.3% by weight of the disintegrant, such as croscarmellose sodium or such as crospovidone.

In some embodiments, the composition further comprises a glidant. In some embodiments, the glidant is colloidal silicon dioxide (also known as anhydrous silicic acid). In other embodiments, the composition comprises about 0.05% to about 3% by weight, or about 0.1% to about 1% by weight, or about 0.1% to about 0.5% by weight, or about 0.1, 0.2, 0.3, 0.4, or 0.5% by weight of the glidant or colloidal silicon dioxide. In some embodiments, the colloidal silicon dioxide has a mean diameter of about 3 to about 4 µm, or about 3 to about 3.5 µm, or about 3.2 µm. In some embodiments, the colloidal silicon dioxide has a pH of about 5.5 to about 8.5, or about 6.0 to about 8.0.

In some embodiments, the composition further comprises a lubricant. In some embodiments, the lubricant is magnesium stearate. In some embodiments, the composition comprises about 0.2% to about 2% by weight, or about 0.2 to about 1% by weight, or about 0.2% to about 0.8% by weight, or about 0.3% to about 0.7% by weight, or about 0.4% to about 0.6% by weight, or about 0.3, 0.4, 0.5, 0.6, or 0.7% by weight.

In some embodiments, the pharmaceutical composition is in a tablet form. In some embodiments, the tablets are formed by dry granulation or direct compression. In some embodiments, the tablets are formed by dry granulation. In other embodiments, the tablets are formed by direct compression. In some embodiments, direct compression tablets are compressed at a hardness of about 3 to about 7 kp, or about 3.5 to about 7 kp, or about 3.5 to about 5.5 kp, or about 4 to about 5 kp, or about 5 kp, or about 6 to about 7 kp, or about 6.6 kp hardness. Target hardness levels are achieved, for example, using a tablet press. U.S. Pharmacopeia (USP) <1217> and European Pharmacopeia (EP) Ch. 2.9.8 describe methods for determining tablet breaking force, commonly referred to as "hardness." Hardness is typically tested using a hardness tester, such as a Schleuniger hardness tester (Pharmatron).

In some embodiments, a mixture of asimadoline or a pharmaceutically acceptable salt thereof and lactose monohydrate, a disintegrant, a glidant, and a lubricant is formed into raw tablets, which may optionally be coated with a tablet coating. In some embodiments, the coating comprises a pigment such as an iron oxide ($Fe_2O_3$). Suitable iron oxides include yellow iron sesquioxide or iron oxide red. In other embodiments, the coating comprises yellow iron sesquioxide. In other embodiments, the coating comprises yellow iron sesquioxide, hypromellose, and titanium oxide. In some embodiments, the coating is about 1% to about 5%, or about 2% to about 4%, or about 2%, 3%, or 4% added weight to the raw tablet. By way of example, a 100 mg total weight raw tablet to which a coating of about 1% to about 5% by weight is added results in a coated tablet weight of about 101 to about 105 mg. In some embodiments, the yellow iron sesquioxide in the coating is about 0.02 to about 3.5%, or about 0.02 to about 0.06%, or about 0.04%, or about 2 to about 4%, or about 2%, or about 3%, or about 4% added weight to the raw tablet.

In some embodiments, coated tablets have a dissolution rate of at least about 88, 89, 90, 91, 92, 93, 94, 95, 96, 97, 98, or 99% after about 15 min, or about 30 min, or about 45 min, as measured in, for example, 900 mL of 0.1 N HCl at 50 rpm paddle speed. In some embodiments, coated tablets have a dissolution rate of at least about 97% at about 15, 30, or 45 min. Dissolution testing is performed according to USP <711>, using Apparatus 2 (paddles). An immediate release profile is characterized by a release rate of greater than 80% dissolved in 1 hour.

In some embodiments, coated tablets have a moisture (water) content of about 4 to about 5.5%, or about 4.5 to about 5%, or about 4.7 to about 5%, or about 4.8% by weight.

In some embodiments, for tablets prior to coating ("raw tablets"), asimadoline or a pharmaceutically acceptable salt thereof (such as the hydrochloride salt) and lactose monohydrate (granulated lactose, spray-dried lactose, or a mixture thereof) together comprise from about 90 to about 98%, or about 93 to about 98%, or about 95 to about 98%, or about 96 to about 97% of the composition by weight. In some embodiments, the raw tablets comprise from about 2 to about 4% by weight of croscarmellose sodium. In some embodiments, the raw tablets comprise about 0.25 to 0.75%, or about 0.4 to about 0.6%, or about 0.5% by weight of magnesium stearate. In other embodiments, the raw tablets comprise about 0.1 to about 0.3%, or about 0.2% of colloidal silicone dioxide.

In some embodiments, raw tablets comprise asimadoline or a pharmaceutically acceptable salt thereof and lactose monohydrate. In some embodiments, the raw tablets further comprise one or more of croscarmellose sodium, colloidal silicon dioxide, and magnesium stearate. In other embodiments, raw tablets comprise asimadoline or a pharmaceutically acceptable salt thereof, lactose monohydrate, and croscarmellose sodium. In other embodiments, raw tablets comprise asimadoline or a pharmaceutically acceptable salt thereof, lactose monohydrate, croscarmellose sodium, and magnesium stearate. In other embodiments, raw tablets comprise asimadoline or a pharmaceutically acceptable salt thereof, lactose monohydrate, croscarmellose sodium, magnesium stearate, and colloidal silicon dioxide. In other embodiments, raw tablets comprise asimadoline or a pharmaceutically acceptable salt thereof, lactose monohydrate, magnesium stearate, and colloidal silicon dioxide. In other embodiments, raw tablets comprise asimadoline or a pharmaceutically acceptable salt thereof, lactose monohydrate, croscarmellose sodium, and colloidal silicon dioxide. In other embodiments, raw tablets comprise asimadoline or a pharmaceutically acceptable salt thereof, lactose monohydrate, magnesium stearate, and colloidal silicon dioxide.

In each embodiment described herein, the composition (e.g., raw tablets or final tablets) lacks microcrystalline cellulose and/or hypromellose. In some embodiments, the composition (e.g., raw tablets or final tablets) lacks microcrystalline cellulose. In other embodiments, the composition (e.g., raw tablets or final tablets) lacks hypromellose. In other embodiments, the composition lacks microcrystalline cellulose and hypromellose (e.g., raw tablets or final tablets). In some embodiments, the raw tablets lack microcrystalline cellulose and hypromellose, but the raw tablet coating comprises hypromellose.

Comparative Formulations

As shown in Comparative Example A below, compositions comprising asimadoline hydrochloride, lactose monohydrate, microcrystalline cellulose (MCC), hypromellose 2910, croscarmellose sodium, and magnesium stearate were prepared using a wet granulation method. However, the resulting tablets were prone to re-hardening, which led to poor disintegration rates after six months to one year of storage, and if disintegrant levels were increased to address re-hardening, the resulting tablets tended to disintegrate during the tablet coating process. In addition, as shown in the Examples section below, the tablets that were produced by this method yielded unacceptable stability results on storage. In addition, MCC was discovered to bind to asimadoline, limiting the ability to test the formulation for drug release properties.

Tablets formed by direct compression or wet granulation with asimadoline hydrochloride and lactose monohydrate in combination with sodium starch glycolate (sodium carboxymethyl starch), cross-linked sodium carboxymethyl starch, cornstarch, or polyvinyl pyrrolidone (e.g., Kollidon® CL) as a disintegrant, hydroxypropyl methylcellulose (hypromellose, e.g., METHOCEL® E15) as a binding agent, magnesium stearate or glyceryl dibehenate (e.g., COMPRITOL® 888 ATO) as a lubricant, and hydrophilic fumed silica (e.g., AEROSIL® 200) as a glidant, yielded formulations with disintegration rates exceeding 15 minutes, which were undesirable for an immediate release dosage form. In particular, tablets prepared by direct compression or wet granulation with lactose monohydrate and one or more of sodium starch glycolate, polyvinyl pyrrolidone, and cornstarch had unacceptably long disintegration rates for an immediate release formulation of from about six to greater than 15 minutes.

Attempts to prepare tablets through direct compression or granulation of calcium hydrogen phosphate based mixtures gave tablets with low breakage and high disintegration rates, low content (75-90%) and low release rates (less than 90% after 30 minutes). Attempted adjuvants for the calcium hydrogen phosphate formulations included carboxymethyl starch sodium salt, carboxy methyl starch sodium cross-linked, Avicel PH200®, polyvinyl pyrrolidone (KOLLIDON® CL), magnesium stearate, and/or AEROSIL® 200.

Additional Embodiments

Pharmaceutical compositions described herein may further comprise one or more additional pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Pharmaceutical compositions may be prepared using compounding techniques known or that become available to those skilled in the art.

The compositions described herein are formulated for oral administration. Such compositions are provided in a solid form, such as a tablet or capsule. In some embodiments, the composition is a tablet form. Oral tablets may include the active ingredient mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

In some embodiments, pharmaceutical compositions according to the invention are sterile compositions, including compositions that are in accord with national and local regulations governing such compositions.

Methods of Making

The invention also relates to methods of making the pharmaceutical compositions described herein. In some embodiments, the method of making comprises: (a) dry blending asimadoline or a pharmaceutically acceptable salt thereof with lactose monohydrate, the disintegrant, and the glidant to form a first blended mixture; (b) milling the first blended mixture (optionally with a cone sieve) to form a milled mixture; (c) dry blending the milled mixture to form a second blended mixture; (d) dry blending the second blended mixture with the lubricant to form a third blended mixture; and (e) compressing the third blended mixture into raw tablets. In some embodiments, the pharmaceutical composition described herein refers to such raw tablets.

In some embodiments, the method of making comprises a direct compression process. In other embodiments, the tablets are formed by a rotary press.

The methods of making optionally further comprise coating the raw tablets to make coated tablets. In such embodiments, the method further comprises: (f) coating the raw tablets, wherein the coating comprises an iron oxide and optionally titanium dioxide.

In some embodiments, particularly for compositions with asimadoline at 0.1 mg to 1.0 mg w/w per tablet, the method includes an additional pre-blend step to improve uniformity, comprising blending asimadoline or a pharmaceutically acceptable salt thereof in a 1:10 w/w ratio with lactose monohydrate to generate an asimadoline mixture that is then used in step (a) above. In some embodiments, the lactose monohydrate used in the pre-blend step is granulated lactose monohydrate.

Methods of Treatment

As used herein, the terms "treat" and "treatment" encompass both "preventative" and "curative" treatment. "Preventative" treatment for a disease or medical condition is meant to indicate a postponement of development of the disease or medical condition, suppressing symptoms of the disease or condition that may appear, or reducing the risk of developing or recurrence of the disease, medical condition, or symptom thereof "Curative" treatment includes reducing the severity of or suppressing the worsening of an existing disease or condition, including a symptom thereof. Thus, treatment includes ameliorating or preventing the worsening of existing disease symptoms, preventing additional symptoms from occurring, ameliorating or preventing the underlying systemic causes of symptoms, inhibiting the condition or disease, e.g., arresting the development of the condition or disease, relieving the condition or disease, causing regression of the condition or disease, relieving a secondary condition caused by the disease or condition, or stopping the symptoms of the disease or condition.

The term "subject" refers to a mammalian patient in need of such treatment, such as a human, or a mammalian pet such as a cat, dog, or horse.

In treatment methods according to the invention, an "effective amount" means an amount or dose sufficient to generally bring about the desired therapeutic benefit in subjects needing such treatment. Effective amounts or doses of the pharmaceutical compositions described herein may be ascertained by routine methods, such as modeling, dose escalation, or clinical trials, taking into account routine factors, e.g., the mode or route of administration or drug delivery, the pharmacokinetics of the agent, the severity and course of the disease or condition, the subject's health status, condition, and weight, and the judgment of the treating physician. An exemplary dose is in the range of from about 0.01 to about 25 mg/kg per dose, or about 0.1 to about 10 mg per dose, or about 0.1 to about 5 mg per dose, or about 0.5 mg per dose, or about 2.5 to about 3.0 mg per dose. In a given day, a patient may be given one, two, three, or four doses (e.g., BID, TID, QID).

Once improvement of the patient's disease or condition, or symptom thereof, has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

A disease or condition mediated by kappa-opioid receptor activity includes, for example, hyperalgesia, inflammation-related hyperalgesia, cerebral edema, hypoxia, ischemic damage, pain, hypersensitivity to pain, neurodermatitis, a disorder of intestinal motility, postoperative ileus, itch, pruritus, an allergic skin disorder, a rheumatic disorder, an inflammatory bowel disorder, irritable bowel syndrome (IBS, including diarrhea-predominant and alternating constipation and diarrhea forms (IBS-D and IBS-A)), diarrhea, nausea, dyspepsia, dyspepsia not associated with an ulcer, a functional intestinal disease, functional abdominal pain, functional wind or flatulence, functional obstipation, constipation, blockage, a chronic motility disorder, neuropathy, peripheral neuropathy, and diabetic neuropathy. In some aspects, the disease or condition mediated by kappa-opioid receptor activity is pruritus or itch. In some embodiments, pruritus or itch is associated with another disease or condition, such as a skin condition or systemic condition. Skin conditions that are associated with pruritus or itch include xerosis, atopic dermatitis, urticarial, psoriasis, arthropod assault, mastocytosis, dermatitis herpetiformis, pemphigoid, dry skin, scabies, eczema, lice, chicken pox, hives, and allergic reactions to external substances (including reactions to poison ivy, wool, chemicals, soaps, cosmetics, and the like). Systemic conditions associated with pruritus or itch include liver disease, celiac disease, kidney failure, iron deficiency anemia, thyroid problems, cancer, leukemia, lymphoma, nervous system disorders, multiple sclerosis, diabetes mellitus, pinched nerves, shingles (herpes zoster), pregnancy, and reactions to ingested substances (such as drugs or food). In some embodiments, the pharmaceutical composition comprises from about 2.5 mg to about 3 mg of asimadoline hydrochloride, for the treatment of pruritus. In some embodiments, the pharmaceutical composition is administered once per day, or is administered twice per day.

Drug Combinations

The pharmaceutical compositions described herein may be used in combination with one or more additional active ingredients. Further additional active ingredients include other therapeutics or agents that are active at the same target as asimadoline, or at a different target associated with the disease, or that mitigate adverse effects. Such combinations may serve to increase efficacy, ameliorate other disease symptoms, decrease one or more side effects, or decrease the required dose of asimadoline to be administered. The one or more additional active ingredients may be administered in a separate pharmaceutical composition or may be included with asimadoline or a pharmaceutically acceptable salt thereof in a single pharmaceutical composition as described herein. The one or more additional active ingredients may be administered simultaneously with, prior to, or after administration of an asimadoline pharmaceutical composition.

For example, suitable active ingredients for combination with the pharmaceutical compositions described herein include medications prescribed for atopic dermatitis, psoriasis, and other skin conditions associated with pruritus or itch, such as steroids, antihistamines, topical anesthetics, topical retinoids, acitretin, anti-inflammatory agents, hydrocortisone, betamethasone, triamcinolone, antihistamines, hydroxyzine, diphenhydramine, immunomodulators, cyclosporine, methotrexate, tacrolimus, azathioprine, mycophenolate, antiviral agents, acyclovir, antibiotics, cephalexin, penicillin (and derivatives thereof), clindamycin, mupirocin, trimethoprim, sulfamethoxazole, non-steroidal anti-inflammatory drugs, TNF-alpha blockers (such as certolizumab pegol, etanercept, adalimumab, infliximab, golimumab, interleukin 12/23, ustekinumab, interleukin 17-A, secukinumab, and apremilast.

EXAMPLES

The following examples are offered to illustrate but not to limit the invention. One of skill in the art will recognize that the following procedures may be modified using methods known to one of ordinary skill in the art.

Example 1. Preparation of Tablets by Dry Blend and Direct Compression

Step 1. Preparation of Raw Tablets.

Raw tablets were produced using the following ingredients and ratios. Asimadoline 2.5 mg tablets contain 2.72 mg of asimadoline hydrochloride (2.5 mg asimadoline free base equivalent).

| Ingredient | Amount (mg/tablet) | Batch Amount (g) 650,000 tablets |
|---|---|---|
| Asimadoline Hydrochloride | 2.72 | 280.0 |
| Lactose monohydrate (Pharmatose 200M) | 9.50 | 978 |
| Lactose monohydrate (SuperTab 11SD) | 84.08 | 8655 |
| Croscarmellose sodium (Ac-Di-Sol) | 3.00 | 309 |
| Magnesium stearate (MF-2-V) | 0.5 | 51 |
| Colloidal silicon dioxide (Cab-O-Sil M5-P) | 0.2 | 21 |
| Total: | 100.0 | 10294 |

A portion of SuperTab 11SD was charged into a 1 cu. ft. V-blender and mixed for 1 min at 18 rpm. Asimadoline HCl (2.5 mg free base equivalent), Pharmatose 200M, croscarmellose sodium, colloidal silicon dioxide, and the remaining SuperTab 11SD were charged sequentially into the V-blender and mixed for 5 min at 18 rpm. The resulting pre-blend was discharged and passed through a Comil 197S cone sieve (813 micron screen, 20 mesh, p/n 2A032R02528), with approximately 1400 rpm impeller speed. The screened material was charged back into the V-blender and mixed for 15 to 30 min at 18 rpm. The drug was uniformly distributed throughout the blend as confirmed by blend uniformity testing. Magnesium stearate was added to the blend, followed by 3 min of lubrication blending. The final blend was compressed into tablets at 2.5 kp, 5 kp, or 6.6 kp hardness on a tablet press (Kikusui Libra, 36 station) with the following in-process limits.

| Parameter | Target | Actual Range |
|---|---|---|
| Tablet Weight | 100 mg | 95-100 |
| Hardness | 5 kp | NLT 4 kp |
| Thickness | 2.7 mm | 2.4-3.0 mm |
| Disintegration | NMT 10 min | |
| Friability | NMT 1.0% after 100 drops | 51 |

*NLT = not lower than; NMT = not more than

Step 2. Preparation of Coated Tablets.

The following ingredients and amounts are used to prepare coated tablets.

| Ingredient | Amount (mg/tablet) | Batch Amount (g) |
|---|---|---|
| Raw Tablets | 100.0 | 10294 |
| Opadry Yellow (03A120007) | 3.0 | 309 |

Raw tablets were coated by spraying with an aqueous suspension of Opadry Yellow (comprising iron sesquioxide yellow) in water using a conventional perforated, side vented coating pan, for example an AQC-100FX coating machine (Freund Corp.) under operating conditions familiar to one of ordinary skill in the art of tablet aqueous film coating. Suitable coating parameter settings for coating formulations of this type and process are known to those skilled in the art and are described in the industry literature. The tablets were coated to a target weight gain of 2%, 3%, or 4%, with a target range of 3-4%.

The final tablets were tested for dissolution in 900 mL of 0.1 N HCl at a paddle speed of 50 rpm. After 15 min, dissolution results of 93.6% (1.9% relative standard deviation (RSD)), 96.9% (2.6% RSD), and 90.8% (2.2% RSD) were obtained for the 2%, 3%, and 4% coated tablets, respectively. After 30 min, dissolution results of 96.6% (0.6% RSD), 99.3% (3.2% RSD), and 96.2% (1.4% RSD) were obtained, and after 45 min, dissolution results of 97.1% (1.1% RSD), 99.2% (1.4% RSD), and 97.1% (1.0% RSD) were obtained for the 2%, 3%, and 4% coated tablets, respectively.

Final 4% coated tablets had a moisture content by Karl Fischer analysis of approximately 4.8% w/w. Dissolution testing of final 4% coated tablets gave 97.3% (0.8%) dissolution at 15 min, 97.7% (1.4% RSD) at 30 min, and 97.4% (0.8% RSD) at 45 min.

Example 2. Preparation of Tablets by Dry Granulation

Step 1: Preparation of Raw Tablets.

Tablets were produced using the following ingredients and ratios.

| Ingredient | Amount (mg/tablet) | Batch Amount (g) 650,000 tablets |
|---|---|---|
| Asimadoline Hydrochloride | 0.5 | 325.0 |
| Lactose monohydrate (Pharmatose 200M) | 9.5 | 6175.0 |
| Lactose monohydrate (SuperTab 11SD) | 86.3 | 56095 |
| Croscarmellose sodium (Kiccolate ND-2HS) | 3.0 | 1950.0 |
| Magnesium stearate | 0.5 | 325.0 |
| Silicic acid (anhydrous) (Adsolider-101) | 0.2 | 130.0 |
| Total: | 100.0 | 65000 |

Asimadoline hydrochloride (0.5 mg asimadoline free base equivalent, provided as asimadoline hydrochloride) and Pharmatose 200M were premixed, and sifted in a cone sieve (Comil QC-197S, Powrex) with a circular impeller, screen at 0.457 mm, and impeller rotational speed of 2400 min$^{-1}$ (frequency, 40 Hz), to form Premixture 1. Alternatively, the mixing can be accomplished with a sieve. Magnesium stearate and Adsolider-101 were each separately premixed with a portion of the SuperTab 11SD. The Adsolider-101/SuperTab 11SD mixture was sifted with a No. 22 sieve (nominal dimension 710 μm). Premixture 1, the magnesium stearate/SuperTabl 11SD mixture, the Adsolider-1/SuperTab 11SD mixture, the remainder of the SuperTab 11SD, and Kiccolate ND-2HS were combined in a Bohle container mixer PM-200 (Kotobuki Engineering & Manufacturing Co., Ltd.) and mixed for 30 min at a rotational speed of 8 rpm to produce Asimadoline Granules.

Asimadoline Granules were formed into 100 mg tablets using an Aquarius C rotary press tableting machine (Kikusui Seisakusho Ltd.), using a pestle and mortar (φ6.5 mm, 9.0R; regular surface), with an agitation feeder, with rotating disk (60 rpm) and stirring blade (30 rpm). Resulting tablets were a hardness of at least 4 kg.

Step 2: Preparation of Coated Tablets.

The following ingredients and amounts are used to prepare coated tablets.

| Ingredient | Amount (mg/tablet) | Batch Amount (g) |
|---|---|---|
| Raw Tablets (0.5 mg active) | 100.0 | 60,000 |
| Hypromellose (TC-5R) | 2.20 | 1430.0 |
| Titanium oxide | 0.76 | 494.0 |
| Yellow iron sesquioxide S | 0.04 | 26.0 |
| Total: | 103.0 | 1950.0 |

TC-5R is dissolved sterile purified water to generate a hypromellose mixture. Titanium oxide and yellow iron sesquioxide S are dispersed in purified water to generate an oxide dispersion. The coating liquid is prepared by sifting the oxide dispersion using a No. 200 sieve (nominal dimensions: 75 um) while adding it to the hypromellose mixture. The resulting coating suspension is applied to the Raw Tablets using a conventional perforated, side vented coating pan, for example an AQC-100FS coating machine (Freund Corp.) under operating conditions familiar to one of ordinary skill in the art of tablet aqueous film coating. Suitable coating parameter settings for coating formulations of this type and process are known to those skilled in the art and are described in the industry literature.

Stability testing of comparable tablets made with mannitol showed an increase in amount of related substances (degradants) relative to the lactose monohydrate formulation. In addition, Kiccolate ND-2HS was found to improve stability of the drug substance in the formulation relative to low-substituted hydroxypropyl cellulose (L-HPC LH-21).

A photostability test was performed to evaluate different amounts of $TiO_2$ in the coating mixture. A level of $TiO_2$ of 0.76 mg per 100 mg tablet was selected based on these results. Further photostability studies revealed that inclusion of yellow iron sesquioxide S in the coating further improved photostability of the drug substance in the tablet formulation. From these results, a level of 0.04 mg of yellow iron sesquioixide S was selected.

Example 3. Evaluation of Magnesium Stearate and Tablet Hardness

Tablets were formed using an agitation feeder from a mixture of the following ingredients:

| Ingredient | Amount (mg/tablet) |
|---|---|
| Asimadoline Hydrochloride | 0.15 |
| Lactose monohydrate (Pharmatose 200M) | 9.85 |
| Lactose monohydrate (SuperTab 11SD) | 86.5 |
| Croscarmellose sodium (Kiccolate ND-2HS) | 3.0 |
| Magnesium stearate | 0.5 |
| Total: | 100.0 |

The resulting tablets had a hardness of 4 kg f.

Comparative control tablets were prepared using a mixture of ingredients as follows

| Ingredient | Amount (mg/tablet) |
|---|---|
| Lactose monohydrate (Pharmatose 200M) | 10.0 |
| Lactose monohydrate (SuperTab 11SD) | 86.8 |
| Croscarmellose sodium (Kiccolate ND-2HS) | 3.0 |
| Magnesium stearate | 0.2 |
| Total: | 100.0 |

The resulting tablets had a hardness of 5 kg. Continuous tableting of this control formulation on a 350,000 tablet (35 kg) scale gave a tablet hardness of approximately 5 kg.

Example 4. Evaluation of Inclusion of Silicic Acid

Tablets (100 mg) were formed using the following ingredients on a 250,000 tablet (25 kg) scale:

| Ingredient | Amount (mg/tablet) |
|---|---|
| Asimadoline Hydrochloride | 0.15 |
| Lactose monohydrate (Pharmatose 200M) | 9.85 |
| Lactose monohydrate (SuperTab 11SD) | 86.3 |
| Croscarmellose sodium (Kiccolate ND-2HS) | 3.0 |
| Magnesium stearate | 0.5 |
| Silicic acid (anhydrous) (Adsolider-101) | 0.2 |
| Total: | 100.0 |

Asimadoline hydrochloride was mixed in a bag with 1900 g of Pharmatose 200M, and sifted through a cone sieve (Comil, screen diameter 0.457 μm). An additional 562.5 g of Pharmatose 200M was sifted through the cone sieve. Adsolider-101 was premixed with SuperTab 11SD and sifted with a 710 μm sieve. Magnesium stearate was premixed with SuperTab 11SD. All materials were mixed in a Bohle container mixer PM-200 (container volume, 100 L) for 30 min at 9 rpm. The tablets produced had a hardness of 6.2 kg. The procedure provided adequate mixing uniformity and drug product uniformity across the batch. The resulting tablets had a hardness of 6.2 kg.

The resulting raw tablets were coated using the method described in Example 1, Step 2, with 2.2 mg TC-5R, 0.76 mg $TiO_2$, and 0.04 mg Yellow iron sesquioxide S per 100 mg tablet, on a 150,000 tablet batch. The resulting tablets had smooth surfaces and uniform coloring.

Example 5. Preparation of 0.03 mg Asimadoline Hydrochloride Tablets

Tablets were prepared in a 210,000 tablet batch according to the method described in Example 4, using the following ingredients:

| Ingredient | Amount (mg/tablet) |
|---|---|
| Asimadoline Hydrochloride | 0.03 |
| Lactose monohydrate (Pharmatose 200M) | 9.97 |
| Lactose monohydrate (SuperTab 11SD) | 86.3 |

-continued

| Ingredient | Amount (mg/tablet) |
|---|---|
| Croscarmellose sodium (Kiccolate ND-2HS) | 3.0 |
| Magnesium stearate | 0.5 |
| Silicic acid (anhydrous) (Adsolider-101) | 0.2 |
| Total: | 100.0 |

Satisfactory drug product uniformity was achieved across the batch.

Example 6. Preparation of 0.5 mg Asimadoline Hydrochloride Tablets

Tablets were prepared in a 225,000 tablet batch according to the method described in Example 4, using the following ingredients:

| Ingredient | Amount (mg/tablet) |
|---|---|
| Asimadoline Hydrochloride | 0.5 |
| Lactose monohydrate (Pharmatose 200M) | 9.5 |
| Lactose monohydrate (SuperTab 11SD) | 86.3 |
| Croscarmellose sodium (Kiccolate ND-2HS) | 3.0 |
| Magnesium stearate | 0.5 |
| Silicic acid (anhydrous) (Adsolider-101) | 0.2 |
| Total: | 100.0 |

Satisfactory drug product uniformity achieved across the batch.

A batch of 650,000 (65 kg) tablets was prepared using the above method. Asimadoline hydrochloride (325.0 g) was mixed in a bag with 3 kg of Pharmatose 200M and put through a Comil sieve (screen diameter, 0.457 μm). The remaining Pharmatose 200M was put through the Comil sieve. Magnesium stearate (325.0 g) was pre-mixed with SuperTab 11SD (3 kg). Adsolider-101 (130.0 g) was pre-mixed with SuperTab 11SD (3 kg) and sifted with a 710 μm sieve. All the materials were combined and mixed for 30 min at a rotational speed of 8 rpm in a Bohle Container Mixer PM-200 (200 L container volume). Tablets were formed using an Aquarius C (Kikusui Seisakush Ltd.) tablet pressure, 10 kN, pre-load, 5 kN, turntable rotational speed, 60 rpm, agitation blade rotational speed, 30 rpm), to a tablet size of φ6.5 mm, 9.0R (regular surface) and a target thickness of 2.7 mm. Satisfactory mixing uniformity and drug product uniformity results were obtained. Tablet hardness was 5.6 kg-6.1 kg (Okada Seiko Co., Ltd.).

The resulting raw tablets (600,000 tablets) were coated using the method described in Example 1, Step 2, with 2.2 mg TC-5R, 0.76 mg $TiO_2$, and 0.04 mg Yellow iron sesquioxide S per 100 mg tablet using an AQC-100FS (Freund Corp.) coating machine. The resulting tablets had smooth surfaces and uniform coloring.

Example 7. Study of Tablet Hardness and Mixing Uniformity

It had been observed that when mixing time was set to 5 minutes, resulting tablets produced initially by agitation feeder had a tablet harness of about 7 kg, but after about 5000 tablets had been produced, tablet hardness had dropped to less than 5 kg. One potential explanation for the variation was insufficient spreading of magnesium stearate, which was exacerbated through use of the agitation feeder. Mixing studies were undertaken to determine how to avoid fluctuations in tablet hardness across batch production. Tablets were prepared on a 250,000 tablet (25 kg) scale with the ingredients listed below, without asimadoline hydrochloride, to evaluate the tablet base for suitable hardness and physical uniformity of the mixture.

| Ingredient | Amount (mg/tablet) |
|---|---|
| Lactose monohydrate (Pharmatose 200M) | 10.0 |
| Lactose monohydrate (SuperTab 11SD) | 86.3 |
| Croscarmellose sodium (Kiccolate ND-2HS) | 3.0 |
| Magnesium stearate | 0.5 |
| Silicic acid (anhydrous) (Adsolider-101) | 0.2 |
| Total: | 100.0 |

Magnesium stearate was premixed with SuperTab 11SD. Adsolider-101 was premixed with SuperTab 11SD and sifted with a 710 μm sieve. Pharmatose 200M, the magnesium stearate/SuperTab 11SD mixture, the Adsolider-101/SuperTab 11SD mixture, remaining SuperTab 11SD, and Kiccolate ND-2HS were put into a Bohle container mixer PM-200 (container volume, 100 L). The resulting material was mixed for 30 minutes with sampling for tablet hardness at 5 min (8.2 kg), 10 min (7.5 kg), and 20 min (6.7 kg), for which tableting was accomplished using an open feeder. After 30 minutes of mixing, tablets were prepared with an open feeder (giving tablets with a 7.1 kg hardness) and with an agitation feeder (giving tablets with a 6.7 kg hardness). Tablet hardness was approximately 7 kg after mixing for 20 min, and further mixing did not cause any further decline in tablet hardness. After 20 min of mixing, small clumps were observed that may have been from magnesium stearate or Adsolider-101, which dissipated after 30 minutes of mixing.

Example 8. Excipient Selection and Stability Studies

A. Uncoated (Raw) Tablets.

The effect of the presence or absence of various excipients on stability of uncoated tablets was examined in the context of wet granulation tablet production methods. Each formulation below contains 0.15 mg asimadoline hydrochloride per tablet. The following ingredients were combined into initial granulated powders and formed into tablets using wet granulation.

| Component | A | B | C | D | E | F | G |
|---|---|---|---|---|---|---|---|
| Pharmatose 200M | 72.65 | 92.85 | 72.65 | 69.65 | 72.65 | 89.85 | 89.85 |
| Ceolus PH-101 (Microcrystalline cellulose) | 20.2 | | | 20.2 | 20.2 | | |

-continued

| Component | A | B | C | D | E | F | G |
|---|---|---|---|---|---|---|---|
| Cornstarch | | | 20.2 | | | | |
| TC-5R (Hypromellose) | 3.0 | 3.0 | 3.0 | 3.0 | | 3.0 | |
| HPC-L (Hydroxypropyl cellulose) | | | | | 3.0 | | 3.0 |
| L-HPC LH-21 (Low-substituted hydroxypropyl cellulose) | | | | 3.0 | | 3.0 | 3.0 |
| Granulated Powder Subtotal: | 96.0 | 96.0 | 96.0 | 96.0 | 96.0 | 96.0 | 96.0 |

Granulated powders A-E were further mixed with the following ingredients.

| Component | A | B | c | D | E | F | G |
|---|---|---|---|---|---|---|---|
| Kiccolate ND-2HS | 3.0 | 3.0 | 3.0 | 3.0 | 3.0 | | |
| L-HPC LH-21 | | | | 3.0 | | 3.0 | 3.0 |
| Magnesium stearate | 1.0 | 1.0 | 1.0 | 1.0 | 1.0 | 1.0 | 1.0 |
| Uncoated Tablets Subtotal: | 100.0 | 100.0 | 100.0 | 100.0 | 100.0 | 100.0 | 100.0 |

The following stability results were obtained for the resulting uncoated tablets. The figures given are total amount of certain related substances as calculated by HPLC.

| Conditions | A | B | C | D | E | F | G |
|---|---|---|---|---|---|---|---|
| 2500 λ, 20 days | 2.81 | 3.27 | 2.20 | 1.96 | 2.22 | 2.99 | 4.12 |
| 60° C., 1 month | 2.55 | 1.58 | 2.84 | 3.74 | 2.31 | | |

In the photostability study, the Pharmatose/cornstarch formulation (C) yielded lower totals for related substances than the Pharmatose/Ceolus (A) or Pharmatose (B) formulations. For the disintegrating agents, L-HPC LH-21 (D) yielded lower related substances than Kiccolate (E). For the binding agents, HPC-L (E) performed better than TC-5R (A). For the heat challenge, Pharmatose (B) performed better than the Pharmatose/cornstarch (C) and Pharmatose/Ceolus (A) mixtures, while Kiccolate (A) performed better than L-HPC LH-21 (D).

To evaluate the effects of TC-5R and HPC-L as binding agents on the stability of the tablets, the following formulations were prepared. Each formulation contained 0.15 mg of asimadoline hydrochloride per tablet.

| Component | H | I |
|---|---|---|
| Pharmatose 200M | 89.85 | 89.85 |
| TC-5R | 3.0 | |
| HPC-L | | 3.0 |
| L-HPC LH-21 | 3.0 | 3.0 |
| Granulated Powder Subtotal: | 96.0 | 96.0 |
| L-HPC LH-21 | 3.0 | 3.0 |
| Magnesium stearate | 1.0 | 1.0 |
| Subtotal Uncoated Tablets: | 100.0 | 100.0 |
| TC-5R | 4.5 | 4.5 |
| Titanium oxide | 1.9 | 1.9 |
| Yellow iron sesquioxide S | 0.1 | 0.1 |
| Macrogol 6000 | 0.5 | 0.5 |
| Total Coated Tablets: | 107.0 | 107.0 |

The following stability results were obtained for the tablets (UC=uncoated; C=coated). The figures given are total amount of certain related substances as calculated by HPLC.

| Conditions | H (UC) | I (UC) | H (C) | I (C) |
|---|---|---|---|---|
| 2500 λ, 20 days | 2.99 | 4.12 | 0.94 | 1.03 |
| 60° C., 1 month | | | 2.98 | 3.86 |

The TC-5R formulation produced lower levels of related substances in the photostability and heat studies. The tablet coating served to reduce the levels of related substances relative to the uncoated tablets for both formulations in the photostability study.

B. Coated Tablets.

The effect of the presence or absence of various coating excipients on stability of coated tablets was examined in the context of wet granulation tablet production methods. Each formulation below contains 0.15 mg of asimadoline hydrochloride per tablet. The following ingredients were used to prepare initial granulated powders that were formed into tablets using wet granulation and coated.

| Component | J | K | L | M |
|---|---|---|---|---|
| Pharmatose 200M | 89.85 | 89.85 | 89.85 | 89.85 |
| TC-5R | 3.0 | 3.0 | 3.0 | 3.0 |
| L-HPC LH-21 | 3.0 | 3.0 | 3.0 | 3.0 |
| Granulated Powder Subtotal: | 96.0 | 96.0 | 96.0 | 96.0 |
| L-HPC LH-21 | 3.0 | 3.0 | 3.0 | 3.0 |
| Magnesium stearate | 1.0 | 1.0 | 1.0 | 1.0 |
| Subtotal in Uncoated Tablets: | 100.0 | 100.0 | 100.0 | 100.0 |
| TC-5R | 2.0 | 2.0 | 4.0 | 4.5 |
| Titanium oxide | 1.0 | 0.95 | 2.0 | 1.9 |
| Yellow iron sesquioxide S | | 0.05 | | 0.10 |
| Macrogol 6000 (PEG) | 0.5 | 0.25 | 1.0 | 0.5 |
| Total in Coated Tablets: | 103.5 | 103.25 | 107.0 | 107.0 |

The following photostability results were obtained for the coated tablets. The figures given are total amount of certain related substances as calculated by HPLC.

| Conditions | H | I | J | K |
| --- | --- | --- | --- | --- |
| 2500 λ, 20 days | 4.65 | 1.61 | 4.34 | 0.94 |

Comparative Example A. Preparation of Tablets by Wet Granulation

Asimadoline tablets are produced by wet granulation using the following ingredients.

| Ingredient | Amount per tablet |
| --- | --- |
| Asimadoline HCl | x mg |
| Lactose monohydrate | 109.2 − x mg (72.8% − y %) |
| Microcrystalline cellulose | 30.3 mg (20.2%) |
| Hypromellose 2910 | 4.5 mg (3%) |
| Water (removed during granulation) | 60 mg |
| Croscarmellose sodium | 4.5 mg (3%) |
| Magnesium stearate | 1.5 mg (1%) |
| Total: | 150.0 mg |

Asimadoline hydrochloride, lactose monohydrate, and microcrystalline cellulose are mixed through 1 mm sieve to produce a granulate base. Hypromellose (METHOCEL® E15) is dispersed in water, and the resulting mixture is stirred for 30 min to ensure complete swelling and dissolution. Once stirring is completed, the solution is allowed to stand so that produced foam subsides. The aqueous hypromellose dispersion is sprayed onto the asimadoline granulate base. The resulting granulate is dehydrated in a WSG fluid bed dryer. Extent of granulation affects the flowability of the granulate, distribution of active substance, and release profile. Croscarmellose sodium and magnesium stearate are mixed and sieved through a 1 mm sieve. The dried granulate and the croscarmellose mixture are mixed in a Turbula mixer. Mixing time is important to ensure even distribution of active substance and adjuvant, with effects on pressability, distribution, and release profile. Tablets are produced using a rotary press.

Tablets are coated in an Accela Cota with a coating liquid prepared from TC-5R (1.695 mg per 150 mg tablet), titanium dioxide.

In a particular example (Comparative Example A1), the wet granulation formulation includes: 0.5 mg asimadoline (in the form of asimadoline hydrochloride), 108.7 mg lactose monohydrate (72%), 30.3 mg microcrystalline cellulose, 4.5 mg hypromellose 2910, 4.5 mg croscarmellose sodium, and 1.5 mg magnesium stearate.

Example 9. Stability Studies

Long-term stability studies were performed on the dry blend formulation of Example 1 and the wet granulation formulation of Comparative Example A1.

| Conditions | Example 1 Degradants (RRT(min), % by HPLC) | Example A1 Degradants (RRT(min), % by HPLC) |
| --- | --- | --- |
| 25° C./60 ± 5% RH (3 months) | All below level of quantitation (0.05%) | RRT(1.27), 0.09<br>RRT(1.33), 0.10<br>RRT(1.36), 0.14<br>RRT(1.74), 0.06<br>RRT(1.92), 0.12<br><br>TOTAL: 0.5 |
| 40° C./75 ± 5% RH (3 months) | All below level of quantitation (0.05%) | RRT(1.27), 0.17<br>RRT(1.33), 0.26<br>RRT(1.36), 0.40<br>RRT(1.74), 0.07<br>RRT(1.93), 0.08<br><br>TOTAL: 1.0 |
| 25° C./60 ± 5% RH (9 months) | All below level of quantitation (0.05%) | Lot A:<br>RRT(0.64), 0.06<br>RRT(0.73), 0.08<br>RRT(0.86), 0.07<br>RRT(1.18), 0.10<br>RRT(1.22), 0.05<br>RRT(1.27), 0.07<br>RRT(1.33), 0.20<br>RRT(1.36), 0.18<br>RRT(1.74), 0.06<br><br>TOTAL: 0.9<br>Lot B:<br>RRT(0.64), 0.05<br>RRT(1.17), 0.10<br>RRT(1.27), 0.05<br>RRT(1.33), 0.14<br>RRT(1.35), 0.19<br>RRT(1.74), 0.07<br><br>TOTAL: 0.6 |
| 25° C./60 ± 5% RH (12 months) | RRT(1.47), 0.05<br>TOTAL: 0.1 | |
| 25° C./60 ± 5% RH (48 months) | | RRT(0.64), 0.08<br>RRT(0.67), 0.14<br>RRT(1.27), 0.21<br>RRT(1.33), 0.96<br>RRT(1.35), 0.70<br>RRT(1.73), 0.06<br><br>TOTAL: 2.2 |

The invention claimed is:

1. A pharmaceutical composition comprising a raw tablet comprising asimadoline or a pharmaceutically acceptable salt thereof, lactose monohydrate, croscarmellose sodium, and magnesium stearate, wherein the raw tablet lacks microcrystalline cellulose and hypromellose, wherein the asimadoline or a pharmaceutically acceptable salt thereof and the lactose monohydrate together are about 90 to about 98% by weight of the composition, and wherein the raw tablet exhibits an immediate release profile characterized by at least 80% dissolution within one hour, as determined by USP<711> dissolution testing.

2. The composition of claim 1, wherein the raw tablet further comprises colloidal silicon dioxide.

3. The composition of claim 1, wherein the raw tablet is coated with a tablet coating comprising an iron oxide pigment.

4. The composition of claim 1, wherein the asimadoline or a pharmaceutically acceptable salt thereof is about 0.25 to about 3.0 mg per tablet and the asimadoline or a pharmaceutically acceptable salt thereof and the lactose monohydrate together are about 93 to about 98%, or about 95 to about 98%, or about 96 to about 97% by weight of the composition.

5. The composition of claim 1, wherein the asimadoline or a pharmaceutically acceptable salt thereof is present at a drug loading of about 1 to about 3% by weight relative to the raw tablet weight.

6. The composition of claim 1, wherein the raw tablet comprises from about 2 to about 4% by weight of croscarmellose sodium.

7. The composition of claim 1, wherein the raw tablet comprises about 0.25 to 0.75%, or about 0.4 to about 0.6%, or about 0.5% by weight of magnesium stearate.

8. The composition of claim 2, wherein the raw tablet comprises about 0.1 to about 0.3%, or about 0.2% of colloidal silicon dioxide.

9. The composition of claim 1, wherein the raw tablet is prepared by dry blending and direct tablet compression.

10. The composition of claim 1, wherein the raw tablet has a dissolution rate of at least about 95, 96, 97, 98, or 99% after about 15, 30, or 45 minutes.

11. The composition of claim 1, wherein the raw tablet has a hardness of about 3 to about 7 kp, or about 3.5 to about 7 kp, or about 3.5 to about 5.5 kp, or about 4 to about 5 kp, or about 5 kp, or about 6 to about 7 kp, or about 6.6 kp hardness.

12. The composition of claim 3, wherein the coated tablet has a dissolution rate of at least about 95, 96, 97, 98, or 99% after about 15, 30, or 45 minutes.

\* \* \* \* \*